(12) United States Patent
Lacheen

(10) Patent No.: US 9,839,897 B2
(45) Date of Patent: Dec. 12, 2017

(54) METHOD FOR REDUCING ORGANIC HALIDE CONTAMINATION IN HYDROCARBON PRODUCTS USING A METAL CHLORIDE

(71) Applicant: Howard Steven Lacheen, Richmond, CA (US)

(72) Inventor: Howard Steven Lacheen, Richmond, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 369 days.

(21) Appl. No.: 13/905,282

(22) Filed: May 30, 2013

(65) Prior Publication Data

US 2014/0357915 A1    Dec. 4, 2014

(51) Int. Cl.
*C07C 2/60* (2006.01)
*B01J 19/24* (2006.01)
(Continued)

(52) U.S. Cl.
CPC ........... *B01J 19/245* (2013.01); *C07C 2/58* (2013.01); *C07C 2/60* (2013.01); *C07C 7/12* (2013.01); *C07C 7/14858* (2013.01); *C10G 29/12* (2013.01); *B01J 2219/24* (2013.01); *C07C 2527/125* (2013.01); *C07C 2531/26* (2013.01); *C10G 2300/305* (2013.01)

(58) Field of Classification Search
CPC ........... C07C 2/62; C07C 2527/1206; C07C 2527/054; C07C 9/16; C07C 2/60; C07C 7/12; C07C 2527/10; C07C 2523/00; C07C 2523/06; C07C 2521/10; C10G 29/205; C10G 29/12

USPC ............... 585/331, 820, 826, 824; 422/187; 208/262.1

See application file for complete search history.

(56) References Cited

U.S. PATENT DOCUMENTS

| 2,481,300 A | 9/1949 | Engel |
| 2,967,819 A | 9/1949 | Leum et al. |

(Continued)

FOREIGN PATENT DOCUMENTS

| JP | 3542055 B2 | 2/1996 |
| JP | 3781871 B2 | 7/1997 |

(Continued)

OTHER PUBLICATIONS

Senderens, Jean B.; Aboulenc, J., The action of the alkaline earth oxides on the monohalogenated methane hydrocarbons, Compt. rend. (1936), 202, 104-6.

(Continued)

*Primary Examiner* — In Suk Bullock
*Assistant Examiner* — Aaron Pierpont
(74) *Attorney, Agent, or Firm* — Susan M. Abernathy

(57) ABSTRACT

We provide a catalytic process to reduce an organic halide in a hydrocarbon, comprising:
  a. producing the hydrocarbon comprising the organic halide in a process unit; and
  b. contacting the hydrocarbon comprising the organic halide with a metal chloride under anhydrous conditions in a halide removal vessel to produce a contacted hydrocarbon having from 50-100 wt % of a total halide in the hydrocarbon removed. We also provide an apparatus for performing this process.

26 Claims, 2 Drawing Sheets

(51) Int. Cl.
*C07C 2/58* (2006.01)
*C07C 7/12* (2006.01)
*C07C 7/148* (2006.01)
*C10G 29/12* (2006.01)

(56) References Cited

U.S. PATENT DOCUMENTS

| | | | |
|---|---|---|---|
| 3,864,243 A | | 2/1975 | Reusser et al. |
| 3,935,295 A | * | 1/1976 | La Hue ............... C01B 7/01 208/226 |
| 4,051,015 A | * | 9/1977 | Bearden et al. ............. 208/108 |
| 4,280,880 A | | 7/1981 | Vora et al. |
| 4,301,137 A | * | 11/1981 | Williams ................ C01B 7/00 201/2.5 |
| 4,721,824 A | | 1/1988 | McWilliams et al. |
| 5,034,566 A | * | 7/1991 | Ishino ..................... C07C 1/30 585/641 |
| 5,371,313 A | | 12/1994 | Ostrowicki |
| 5,379,705 A | * | 1/1995 | Takada ................. F23G 5/30 110/229 |
| 5,672,266 A | * | 9/1997 | Sivik .................... A62D 3/34 208/262.1 |
| 5,928,500 A | | 7/1999 | Richard et al. |
| 6,060,033 A | * | 5/2000 | Cheng ................ B01D 53/02 423/240 S |
| 6,432,374 B1 | | 8/2002 | Takase et al. |
| 7,432,408 B2 | | 10/2008 | Timken et al. |
| 7,495,144 B2 | | 2/2009 | Elomari |
| 7,531,707 B2 | | 5/2009 | Harris et al. |
| 7,569,740 B2 | | 8/2009 | Elomari |
| 7,732,654 B2 | | 6/2010 | Elomari et al. |
| 8,067,656 B2 | | 11/2011 | Luo et al. |
| 2007/0009423 A1 | * | 1/2007 | Handy et al. ................. 423/497 |
| 2009/0163759 A1 | * | 6/2009 | Driver ..................... C07C 2/60 585/826 |
| 2009/0264694 A1 | * | 10/2009 | Driver ..................... C07C 2/58 585/713 |

FOREIGN PATENT DOCUMENTS

| | | |
|---|---|---|
| JP | 2007190503 A | 1/2006 |
| JP | 2008184512 A | 1/2007 |

OTHER PUBLICATIONS

Senderens, Jean B., Catalytic decomposition of monochloromethane derivatives, Compt. rend. (1935), 200, 612-15.

Peter V Broadhurst, Removal of chloride compounds, Petroleum Technology Quarterly, 2003 / Q2, Spring 2003, p. 127-135.

Haibo Zhao, Johnathan E. Holladay, Heather Brown, Z. Conrad Zhang, Metal Chlorides in Ionic Liquid Solvents Convert Sugars to 5-Hydromethylfurfural.

* cited by examiner

METHOD FOR REDUCING ORGANIC HALIDE CONTAMINATION IN HYDROCARBON PRODUCTS USING A METAL CHLORIDE

TECHNICAL FIELD

This application is directed to a method for reducing organic halide contamination in hydrocarbon products by contacting a hydrocarbon fraction comprising an organic halide contaminant with metal chloride under anhydrous conditions.

BACKGROUND

Alternative and improved methods for reducing organic halide contaminants in hydrocarbon products produced by ionic liquid catalyzed hydrocarbon conversion reactions are desired.

SUMMARY

This application provides a catalytic process to reduce an organic halide in a hydrocarbon, comprising:
 a. producing the hydrocarbon comprising the organic halide in a process unit; and
 b. contacting the hydrocarbon comprising the organic halide with a metal chloride under anhydrous conditions in a halide removal vessel to produce a contacted hydrocarbon having from 50-100 wt % of a total halide in the hydrocarbon removed.

This application also provides an apparatus for making a hydrocarbon with a reduced amount of an organic halide, comprising:
 a. a process unit that produces a hydrocarbon comprising an organic halide; and
 b. a halide removal vessel, in which the hydrocarbon comprising the organic halide is contacted with a metal chloride under anhydrous conditions to produce a contacted hydrocarbon having from 50-100 wt % of a total halide in the hydrocarbon removed.

The present invention may suitably comprise, consist of, or consist essentially of, the elements a and b, as described above.

DETAILED DESCRIPTION

Figure 1:
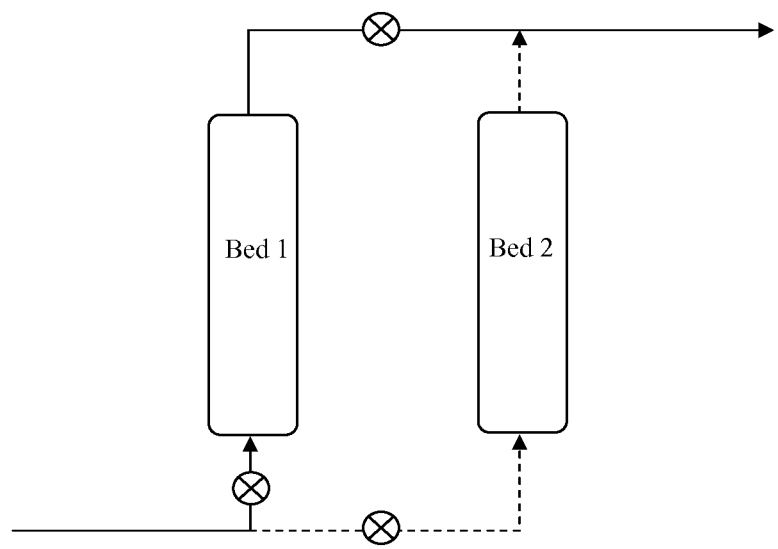
FIG. 1 is a diagram of a parallel arrangement of halide removal vessels.

The hydrocarbon comprising the organic halide can be made in various process units using different catalysts and processes. The process unit can perform, for example, isoparaffin alkylation with olefins; oligomerization of olefins to make distillate, base oil or polymers; paraffin dis-proportionation; aromatic alkylation; aromatic trans-alkylation; acetylation; metatheses; and co-polymerization.

The term 'anhydrous' means that there is essentially no water present. For example, the amount of water present can be from zero to 20 wppm.

Hydrocarbon Comprising an Organic Halide

Examples of these hydrocarbons include alkylate products, oligomerization products, or mixtures thereof. In one embodiment the hydrocarbon comprising the organic halide comprises a gasoline blending component, a middle distillate, a lubricant, or a mixture thereof. Gasoline blending components can be blended into gasoline or used directly as gasoline. Examples of gasoline blending components are naphtha and heavy naphtha. In the context of this disclosure, naphtha has a boiling range distribution less than 130° C. and heavy naphtha has a boiling range distribution from 130 to 200° C. In one embodiment, the gasoline blending component has a high octane number. In this embodiment, the gasoline blending component can have a RON from 80-105. Examples of high octane numbers are 82 or higher, 85 or higher, 90 or higher, and 95 or higher. Different methods are used for calculating octane numbers of fuels or fuel blend components. The Research-method octane number (RON) is determined using ASTM D 2699-07a. The test for measuring RON employs the standard Cooperative Fuel Research (CFR) knock-test engine. Additionally, the Research-method octane number can be calculated [RON (GC)] from gas chromatography boiling range distribution data. The RON (GC) calculation is described in the publication, Anderson, P. C., Sharkey, J. M., and Walsh, R. P., "Journal Institute of Petroleum", 58 (560), 83 (1972).

A "middle distillate" is a hydrocarbon product having a boiling range between 250 to 735° F. (121° to 391° C.). The term "middle distillate" includes the diesel, heating oil, jet fuel, and kerosene boiling range fractions. It can also include a portion of naphtha or light oil. In the context of this disclosure, a "base oil" is a hydrocarbon boiling in the range of about 650° F. (343 degree Celsius) and higher. Base oils can be blended with additives and used, for example, as diluents for the additives or in finished lubricants.

The test methods used for boiling range distributions of the hydrocarbons in this disclosure are ASTM D 2887-06a and ASTM D 6352-04. The boiling range distribution determination by distillation can be simulated by the use of gas chromatography. The boiling range distributions obtained by gas chromatography are essentially equivalent to those obtained by true boiling point (TBP) distillation (see ASTM Test Method D 2892), but are not equivalent to results from low efficiency distillations such as those obtained with ASTM Test Methods D 86 or D 1160.

In one embodiment, the hydrocarbon is an alkylate gasoline blending component that has a RON that is from 0 to 1.0 different from a contacted RON of the contacted hydrocarbon. In this embodiment, the contacting with the metal chloride does not degrade the quality of the alkylate gasoline blending component.

In one embodiment the hydrocarbon is saturated, with no double bonds. In another embodiment, the hydrocarbon and the contacted hydrocarbon are saturated. In another embodiment, the hydrocarbon, the contacted hydrocarbon, or both can be unsaturated. Examples of saturated hydrocarbons include C2-C60 hydrocarbons, such as n-butane, n-pentane, and trimethylpentane.

In one embodiment, the hydrocarbon comprising the organic halide can be produced in a process unit comprising an ionic liquid catalyst comprising an anhydrous metal chloride.

Process Unit

The process unit can be any set of equipment or a reactor that is used to produce the hydrocarbon comprising the organic halide. The process unit is designed to handle the hydrocarbon feeds, to perform the desired catalytic function on the feeds, as well as to discharge the hydrocarbon comprising the organic halide. It can have reactor inlet ports, a reactor chamber, and effluent ports. In one embodiment, the process unit additionally comprises an alkyl halide or a hydrogen halide. Alkyl halides and hydrogen halides can be used as promoters for the ionic liquid or other acid catalyst. Examples of processes using anhydrous HCl are described in co-owned U.S. Pat. No. 7,432,408. Examples of processes using alkyl halide promoters are described in co-owned U.S. Pat. Nos. 7,495,144 and 7,531,707. In one embodiment, the alkyl halide comprises a C2-C10, or a C2-C6, alkyl halide. When alkyl halide is used as a promoter, HCl can be formed in situ in the process unit. In one embodiment, the alkyl halide comprises a C2-C6 alkyl halide.

Ionic Liquid Catalyst

Ionic liquids are generally organic salts with melting points below 100° C., and often below room temperature. They can find applications in various chemical reactions, solvent processes, and electrochemistry. Ionic liquid catalysts can be used for a wide variety of chemical reactions, including alkylation, dimerization, oligomerization, acetylation, metatheses, and co-polymerization. The ionic liquid catalyst of this invention comprises an anhydrous metal chloride. Examples of anhydrous metal chlorides that can be used include $AlCl_3$, $TiCl_4$, $SnCl_4$, and $FeCl_3$. Anhydrous metal chlorides are used because the ionic liquid catalysts comprising the anhydrous metal chlorides are highly water reactive and can be dangerous to use when water is present.

Most ionic liquids are prepared from organic cations and inorganic or organic anions. Cations include, but are not limited to, ammonium, phosphonium and sulphonium. Anions include, but are not limited to: $BF_4-$, $PF_6-$, haloaluminates such as $Al_2Cl_2-$, $Al_3Cl_{10}-$, and $Al_2Br_7-$, $[(CF_3SO_2)2N]-$, alkyl sulfates ($RSO_3-$), and carboxylates ($RCO_2-$).

In one embodiment, the ionic liquid catalyst comprising an anhydrous metal chloride is chloroaluminate ionic liquid catalyst. The use of chloroaluminate ionic liquids as alkylation catalysts in petroleum refining has been described, for example, in commonly assigned U.S. Pat. Nos. 7,531,707, 7,569,740, and 7,732,654.

In one embodiment, the ionic liquid catalyst is a quaternary ammonium chloroaluminate ionic liquid salt. Examples of quaternary ammonium chloroaluminate ionic liquid salts are an N-alkyl-pyridinium chloroaluminate, an N-alkyl-alkylpyridinium chloroaluminate, a pyridinium hydrogen chloroaluminate, an alkyl pyridinium hydrogen chloroaluminate, a di-alkyl-imidazolium chloroaluminate, a tetra-alkyl-ammonium chloroaluminate, a tri-alkyl-ammonium hydrogen chloroaluminate, or a mixture thereof.

For example, a typical reaction mixture to prepare n-butyl pyridinium chloroaluminate ionic liquid salt is shown below:

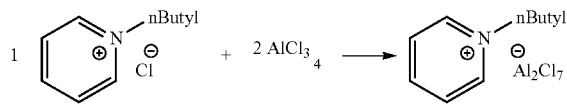

Metal Chloride

The hydrocarbon comprising the organic halide is contacted with a metal chloride. The metal chloride can be the same or different from the anhydrous metal chloride that is in the ionic liquid catalyst used in the process unit to produce the hydrocarbon. The metal chloride can be any chloride salt of alkaline earth metals or transition metals in Groups 1, 2, and 4-12 of the IUPAC Periodic Table of the Elements dated Jun. 1, 2012. Examples of metal chlorides that can be used comprise barium chloride, calcium chloride, zinc chloride, magnesium chloride, iron chloride, chromium chloride, copper chloride, or a mixture thereof.

The contacting with the metal chloride produces the contacted hydrocarbon having a reduced amount of an organic halide, and from 50-100 wt % of the total halide in the hydrocarbon is removed. In other embodiments, from 70-100 wt %, from 80-100 wt %, or even from 90-100 wt % of the total halide in the hydrocarbon is removed. In one embodiment, the process for removing the organic halide is different from absorption or adsorption. In this embodiment, the metal chloride functions as a catalyst and the efficacy for removing the total halide improves with increasing temperature. One benefit of the metal chloride functioning as a catalyst is that the metal chloride can be used for an extended time, or continuously, without reactivation. Without being bound by theory, we suspect the catalytic reaction can be:

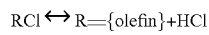

The organic chloride, or other organic halide, decomposes readily in the presence of the metal chloride (e.g., calcium chloride) under anhydrous conditions and at a temperature from 50° C. to 400° C. The contacting can also generate significant amounts of HCl gas. In one embodiment, the HCl gas is vented. In another embodiment, the HCl gas is removed from the halide removal vessel using a purge gas. In yet another embodiment, the HCl gas is absorbed onto a suitable absorbent. Maintaining a low concentration of the HCl in the halide removal vessel facilitates the continued conversion of RCl to R=.

In one embodiment, the halide removal vessel comprises both a metal chloride and a metal oxide. The metal oxide can be present on an absorbent used to remove chloride, for example. Metal oxides are effective for decomposing organic chlorides at elevated temperature by absorbing HCl produced by the decomposition reaction. As the metal oxide absorbs the HCl, some of the metal oxide is converted to metal chloride in the halide removal vessel and the metal chloride becomes active for contacting the hydrocarbon to further reduce the organic halide in the hydrocarbon.

Organic Halide

The organic halide in the hydrocarbon can be present in an amount that is substantial and undesirable. Organic halide can contribute to corrosion of equipment, and can form unwanted byproducts during subsequent use or combustion. In different embodiments, the total halide in the hydrocarbon is from 20 to 100 wppm, 50 to 5,000 wppm, 100 to 4,000 wppm, or 75 to 2,500 wppm. In one embodiment, the organic halide in the hydrocarbon product is an organic chloride. The organic chloride may comprise one or more alkyl chlorides, e.g., a C2-C60 alkyl chloride. In one embodiment, the organic chloride comprises a C4-C16 organic chloride.

Separating

In one embodiment, the hydrocarbon is separated from an ionic liquid catalyst prior to contacting the hydrocarbon with the metal chloride. Any separator that effectively does this can be used. Examples of separators include coalescers, decanters, centrifuges, separating columns, and filters. Examples of effective coalescing separators that can be used are described in co-owned U.S. Pat. No. 8,067,656.

In one embodiment, the apparatus for making a hydrocarbon with a reduced amount of an organic halide comprises:

a. a process unit, containing an ionic liquid catalyst comprising an anhydrous metal chloride, that produces the hydrocarbon comprising the organic halide;

b. a separator that separates the hydrocarbon comprising the organic halide from the ionic liquid catalyst; and c. a halide removal vessel, in which the hydrocarbon comprising the organic halide that has been separated from the ionic liquid catalyst is contacted with a metal chloride under anhydrous conditions to produce a contacted hydrocarbon having from 50-100 wt % of a total halide in the hydrocarbon removed.

In one embodiment, the halide removal vessel also contains an adsorbent or other material that selectively removes HCl, thus producing the contacted hydrocarbon without HCl and having from 50-100 wt % of a total halide in the hydrocarbon removed.

Contacting

In one embodiment, the contacting of the hydrocarbon comprising the organic halide with the metal halide is done under anhydrous conditions in a halide removal vessel. The halide removal vessel can be a chloride removal vessel, for example. By anhydrous is meant that from 0 to 20, or from 0 to 5, wppm water is present in the halide removal vessel where the contacting occurs. The anhydrous conditions prevent the metal halide from becoming hydrolyzed into less active catalysts for organic chloride removal. The level of water can be controlled to higher or lower levels depending on the metallurgy used in the halide removal vessel.

In one embodiment, metal oxide, metal hydroxide, or metal carbonate are converted in the presence of HCl under the anhydrous conditions in the halide removal vessel. Examples of these materials include calcium oxide, calcium hydroxide, or calcium carbonate, which are converted to calcium chloride in the presence of HCl under the anhydrous conditions in the halide removal vessel. The calcium oxide, calcium hydroxide, or calcium carbonate can be components in adsorbents comprising mixed metal oxides.

In one embodiment, the metal chloride is produced from an adsorbent comprising a metal oxide. In one embodiment, the adsorbent comprising a metal oxide comprises from 5 to 75 wt % CaO, or 30 to 60 wt % CaO. In one embodiment, the adsorbent comprising a metal oxide comprises both CaO and ZnO or both CaO and MgO. The adsorbent can either be supported or unsupported. When used, typical supports include various kinds of carbon, alumina, and silica. In one embodiment, the adsorbent is supported on clay. Examples of clays are montmorillonite, bentonite, kaolin, gairome, and kibushi. The activity of the adsorbent for removing chloride does not decline with the formation of the $CaCl_2$ in the adsorbent, indicating that $CaCl_2$ contributes to the removal of the organic chloride from the hydrocarbon. The presence of the $CaCl_2$ in the adsorbent can extend the activity of the adsorbent comprising the metal oxide.

The conditions for the contacting can include one or more of the following, a contacting temperature from 50° C. to 400° C., a liquid hourly space velocity (LHSV) from 0.5 to 20 $hr^{-1}$, a mass ratio of the hydrocarbon to the metal chloride from 0.5 to 200, a pressure of 20 to 5000 kPa, and a contact time of one to 4320 minutes (0.017 to 72 hours), or 9 to 2160 minutes (0.15 to 36 hours). In one embodiment the contacting temperature is from 50° C. to less than 225° C. In another embodiment, the contacting temperature is from 100° C. to less than 225° C. In yet another embodiment, the contacting temperature is less than 205° C. A liquid hourly space velocity (LHSV) from 0.5 to 20 $hr^{-1}$ can be used in a continuous system. A mass ratio of the hydrocarbon to the metal chloride from 0.5 to 200 can be used in a batch system.

In one embodiment, the hydrocarbon is fed directly to the halide removal vessel from a treatment that heats the hydrocarbon to the contacting temperature. An example of this is from an isostripper column, such as described in U.S. Pat. No. 4,280,880, where the hydrocarbon effluent from the isostripper column has a contacting temperature of 275° F. (135 degree Celsius) to 400° F. (204.4 degree Celsius). In this embodiment, additional heating and compression for the halide removal vessel can be reduced or entirely eliminated.

In one embodiment, the hydrocarbon comprises 50 to 5,000 wppm of the total chloride and the contacted hydrocarbon comprises from zero to 10 wppm of the total chloride.

In another embodiment, the hydrocarbon comprises from 20 to 100 wppm of the total chloride and the contacted hydrocarbon comprises from zero to 5 wppm of the total chloride.

Figure 2:
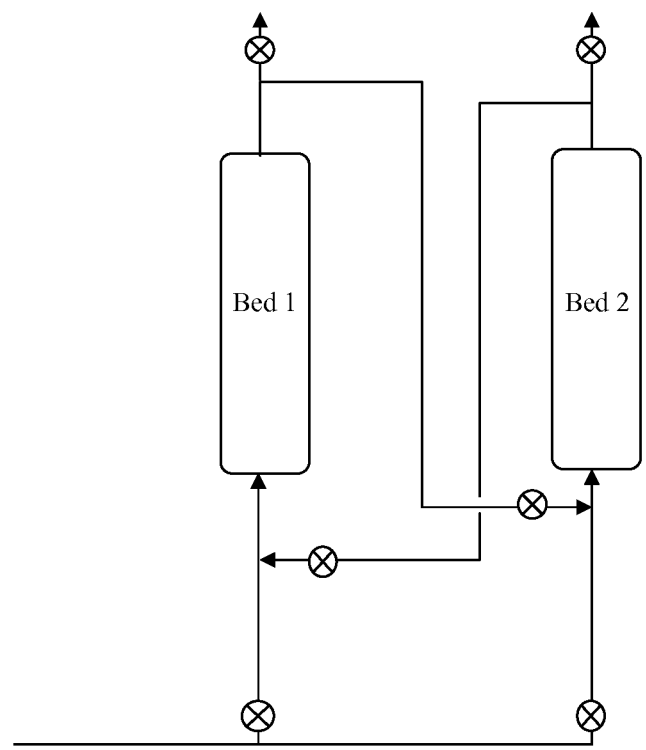
FIG. 2 is a diagram of a series arrangement of halide removal vessels.

The contacting can occur in two or more beds, wherein one bed can be used for the contacting while a different bed can be re-charged with the metal chloride or used in a cascading arrangement. This feature is demonstrated in FIGS. 1 and 2. In FIG. 1, two halide removal vessels are arranged in parallel, where one is used at a time. In FIG. 2, two halide removal vessels are arranged in a series, where one of the halide removal vessels follows another. This series arrangement can be used to remove the organic halide contaminants in a step-wise fashion to lower and lower levels. In one embodiment, the series arrangement of vessels can include additional halide removal vessels, such as from three to ten, to obtain the contacted hydrocarbon having a higher wt % of the total halide in the hydrocarbon removed. In one embodiment, the hydrocarbon passes through a freshest bed last. The freshest bed means that the metal chloride was most recently re-charged to that bed compared to others being used for the contacting.

In one embodiment, the contacting occurs in two or more beds wherein one bed is used for the contacting while a different bed is re-charged with the metal chloride or operated in standby. When 'operated in standby', the different bed is kept in readiness to serve as a substitute bed for contacting, if and when it is needed.

The halide removal vessels used for the contacting are made from various materials, including those that are resistant to chloride corrosion, and those that are less resistant to chloride corrosion. Because the conditions in the halide removal vessel are anhydrous, chloride corrosion is much less likely to occur. Steels with higher levels of chromium, nickel, molybdenum and nitrogen increase resistance to localized corrosion and can be used, but are not necessary. Other materials that could be used include carbon steel, stainless steel, aluminum, glass, polymers, or plastics. Specific examples of steel materials that can be used are the HASTELLOY® corrosion resistant alloys trademarked by Haynes International, Inc. Another example of a corrosion resistant alloy that can be used is MONEL® alloy. MONEL® is a trademark of Special Metals Corporation for a series of nickel alloys, primarily composed of nickel (up to 67%) and copper, with some iron and other trace elements.

In one embodiment, the contacting occurs as a polishing step after a first chloride removal step. The first chloride removal step could be one or more of the following: caustic wash, hydrodechlorination, another catalytic dechlorination, or absorption, for example.

In another embodiment, the contacting occurs before a finishing step, using a caustic wash or a bed of potassium hydroxide (KOH), to further treat the contacted hydrocarbon.

EXAMPLES

Example 1

Ionic Liquid Catalyst Comprising Anhydrous Metal Chloride

Various ionic liquid catalysts made of metal chlorides such as $AlCl_3$, $GaCl_3$, and $InCl_3$ could be used in the alkylation process unit. N-butylpyridinium chloroaluminate ($C_5H_5C_4H_9Al_2Cl_7$) ionic liquid catalyst is an example of a catalyst used in our alkylation process units to make an alkylate gasoline blending component. The ionic liquid catalyst had the following composition:

| | |
|---|---|
| Wt % Al | 12.4 |
| Wt % Cl | 56.5 |
| Wt % C | 24.6 |
| Wt % H | 3.2 |
| Wt % N | 3.3 |

Example 2

Alkylation of $C_4$ Olefin and Isobutane to Make Alkylate Gasoline Blending Component in Pilot Plant Evaluation of $C_4$ olefins alkylation with isobutane was performed in a continuously stirred tank reactor using typical refinery mixed $C_4$ olefin feed and isobutane. An 8:1 molar mixture of isobutane and olefin was fed to the reactor while vigorously stirring. The ionic liquid catalyst described in Example 1 was fed to the reactor via a second inlet port targeting to occupy 6 vol % in the reactor. A small amount of n-butyl chloride was added to produce anhydrous HCl gas. The average residence time (combined volume of feeds and catalyst) was about 6 minutes. The outlet pressure was maintained at 200 psig and the reactor temperature was maintained at 95° F. (35° C.) using external cooling.

A sample of fully saturated alkylate gasoline blending component produced in the pilot plant was analyzed by X-ray fluorescence (XRF) for total chlorides and analyzed by GC to calculate the RON and to measure the wt % trimethylpentane (wt % TMP) in the C8 fraction. The results are shown below.

| | Alkylate Gasoline Blending Component |
|---|---|
| Total Chlorides, wppm (XRF) | 455 |
| RON (GC) | 90.7 |
| Wt % TMP in C8 Fraction (GC) | 83 |

Example 3

Organic Chloride Reduction at Elevated Temperature (Comparative Case)

To examine the effect of heating without a metal chloride on chloride removal in a hydrocarbon, a base case experiment was performed. 100 g of the alkylate gasoline blending component from Example 2, containing 455 wppm total chlorides by XRF, was placed in a 300 mL HASTELLOY® C-276 Parr autoclave. The autoclave was purged with dry nitrogen before heating, to ensure anhydrous conditions in the autoclave. The alkylate gasoline blending component was heated to 200° C. while stirring, and then held at that temperature for twelve hours. The alkylate gasoline blending component was cooled to room temperature, to approximately 25° C. The contacted alkylate gasoline blending component had 392 wppm chloride, which corresponded to a 14 wt % reduction in total chloride from the starting alkylate gasoline blending component.

Example 4

Organic Chloride Reduction with Calcium Chloride

Anhydrous calcium chloride (99%+purity) was purchased from Aldrich and used without any treating. 50 mL of the alkylate gasoline blending component from Example 2 and 5.026 g of calcium chloride were loaded into a 300 mL HASTELLOY® C-276 Parr autoclave. The mixture of alkylate gasoline blending component and calcium chloride was heated to 200° C. while stirring, and then held at that temperature for twelve hours. The autoclave was cooled to room temperature and the contacted hydrocarbon was filtered to obtain clean contacted alkylate gasoline blending component. The contacted alkylate gasoline blending component had 1 wppm chloride, which corresponded to 99.8 wt % reduction in total chloride from the starting alkylate gasoline blending component. Notably, in this experiment there was no adsorbent material in the autoclave and the chloride reduction was orders of magnitude higher than that obtained in the base case shown in Example 3.

Results of Examples 3 and 4 are compared in the following table.

| Catalyst | Catalyst Amount, g | Alkylate, g | Temperature in Chloride Removal Vessel | Total Choride, wppm by XRF | Wt % Chloride Removed | RON (GC) |
|---|---|---|---|---|---|---|
| None | 0 | — | As produced | 455 | Base | 90.7 |
| None | 0 | 100 | 200° C. | 392 | 14 | 90.7 |
| $CaCl_2$ | 5.026 | 50 | 200° C. | 1.0 | 99.8 | 90.6 |

The contacted alkylate gasoline blending component had a contacted RON that was only 0.1 different from the original alkylate gasoline blending component. The contacting with the metal chloride caused no degradation of the alkylate gasoline blending component.

Example 5

Oxide Based Adsorbents/Absorbents

Various oxides of metals were prepared and/or purchased to compare their abilities to reduce organic chloride in hydrocarbons.

These materials had the following compositions:

| | |
|---|---|
| $Fe_2O_3$ | Aldrich, 99+% |
| ZnO | Aldrich, 99+% |
| CaO | Prepared by Calcining $CaCO_2$ at 850° C. |
| MgO | MgO (dried at 350° C.) |

Example 6

Comparison of Calcium Chloride vs. Oxide Based Adsorbent for Organic Chloride Reduction The fully saturated feed alkylate containing 455 ppm total chlorides by XRF was placed in a 300 mL HASTELLOY® C-276 Parr autoclave and contacted with varying amounts and compositions of oxides and chlorides of metals. The autoclave was purged with dry nitrogen before heating, to ensure anhydrous conditions in the autoclave. The mixtures of the alkylate and test materials were controlled to a contacting temperature of 200° C., and they were stirred for twelve hours. The conditions and results achieved are summarized below.

| Test Material | Alkylate (g) | Adsorbent (g) | Mass Ratio Alkylate/Adsorbent | Chloride, wppm by XRF | Wt % Chloride Removed | RON (GC) After Contacting |
|---|---|---|---|---|---|---|
| Base Case | — | 0 | — | 455 | Base | 90.7 |
| $Fe_2O_3$ | 50 | 5.012 | 10 | 234 | 48.7 | 90.7 |
| ZnO | 50 | 5.063 | 10 | 174 | 61.8 | 90.6 |
| CaO | 50 | 2.009 | 24.9 | 138 | 69.7 | 90.7 |
| MgO | 50 | 5.013 | 10 | 0.9 | 99.8 | 90.7 |
| $CaCl_2$ | 50 | 5.026 | 10 | 1.0 | 99.8 | 90.6 |
| $MgCl_2$ | 50 | 5.006 | 10 | 105 | 77.0 | 91.0 |

Even in the absence of an absorbent material, 14 wt % of the total chloride was reduced by the 12 hour test.

The contacting with the metal oxides in the table above showed reduction of organic chloride in the range of 48.7-99.8 wt %. The primary mechanism for organic chloride reduction by contacting with metal oxides was high temperature decomposition followed by adsorption of HCl.

As shown in Example 4, and in the above table, the $CaCl_2$ removed 99.8 wt % of the total chloride in the alkylate gasoline blending component by a catalytic process. The chloride removal by the $CaCl_2$ in the alkylate gasoline blending component was as good as or better than the chloride removal by any other commercial adsorbents that were tested. The contacting with the $MgCl_2$ gave greater than 75 wt % of the total halide in the hydrocarbon removed, and provided a contacted RON that was higher than the RON of the hydrocarbon before contacting.

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof.

The invention illustratively disclosed herein suitably may be practiced in the absence of any element which is not specifically disclosed herein.

It is claimed:

1. A catalytic process to reduce a content of an organic chloride in a stream comprising a hydrocarbon and an organic chloride, comprising:
   a) producing the stream comprising the hydrocarbon and the organic chloride in a process unit; and b) contacting the stream comprising the hydrocarbon and the organic chloride with both a metal chloride catalyst and a metal oxide in a halide removal vessel under anhydrous conditions at a temperature of from 50° C. to less than 225° C. to decompose the organic chloride and produce an effluent comprising HCl gas and a contacted saturated hydrocarbon that is a gasoline blending component, a middle distillate, or a base oil, wherein:

the metal oxide absorbs the HCl gas;

the stream comprising the hydrocarbon and the organic chloride has a total chloride content and the contacted saturated hydrocarbon has a lower total chloride content that is less than the total chloride content by 50 to 100 wt %; and the contacting with the metal chloride does not comprise absorption or adsorption of the organic chloride.

2. The catalytic process of claim 1, wherein the hydrocarbon is saturated.

3. The catalytic process of claim 1, wherein the total chloride content in the stream comprising the hydrocarbon and the organic chloride is 75wppm to 2500 wppm.

4. The catalytic process of claim 1, wherein the process unit comprises an ionic liquid catalyst and an alkyl chloride.

5. The catalytic process of claim 4, wherein the alkyl chloride comprises a C2-C6 alkyl chloride.

6. The process of claim 1, wherein the organic chloride comprises a C4-C16organic chloride.

7. The catalytic process of claim 4, wherein the ionic liquid catalyst is a chloroaluminate ionic liquid catalyst.

8. The catalytic process of claim 7, where the chloroaluminate ionic liquid catalyst is a quaternary ammonium chloroaluminate ionic liquid salt.

9. The catalytic process of claim 1, wherein the metal chloride catalyst comprises calcium chloride, magnesium chloride, iron chloride, chromium chloride, zinc chloride, copper chloride, or a mixture thereof.

10. The catalytic process of claim 1, wherein the gasoline blending component is an alkylate gasoline.

11. The catalytic process of claim 10, wherein the alkylate gasoline has a first RON, the stream comprising the hydrocarbon and the organic chloride has a second RON, and the first RON and the second RON differ by from 0 to 1.0.

12. The catalytic process of claim 1, wherein the temperature during the contacting is from 100° C. to less than 225° C.

13. The catalytic process of claim 1, wherein the temperature during the contacting is from 50° C. to less than 205° C.

14. The catalytic process of claim 1, wherein a liquid hourly space velocity during the contacting is from 0.5 to 20 $hr^{-1}$.

15. The catalytic process of claim 1, wherein a mass ratio of the hydrocarbon to the metal chloride during the contacting is from 0.5 to 200.

16. The catalytic process of claim 1, wherein the hydrocarbon is fed directly to the halide removal vessel from a treatment that heats the hydrocarbon to the contacting temperature used during the contacting.

17. The catalytic process of claim 1, wherein the contacting occurs for a contact time from 0.15 to 36 hours.

18. The catalytic process of claim 1, wherein the total chloride content of the stream comprising the hydrocarbon the and the organic chloride is from 50 to 5,000 wppm and the lower total chloride content of the contacted saturated hydrocarbon is from zero to 10 wppm.

19. The catalytic process of claim 1, wherein the total chloride content of the stream comprising the hydrocarbon and the organic chloride is from 20 to 100 wppm and the lower total chloride content of the contacted saturated hydrocarbon is from zero to 5 wppm.

20. The catalytic process of claim 1, wherein the lower total chloride content is less than the total chloride content by 90-100 wt %.

21. The catalytic process of claim 1, wherein the contacting occurs in two or more beds, wherein one bed is used for the contacting while a different bed is re-charged with the metal chloride catalyst.

22. The catalytic process of claim 21, wherein the stream comprising the hydrocarbon and the organic chloride passes through a freshest bed last.

23. The catalytic process of claim 1, wherein the metal chloride catalyst is produced from an adsorbent comprising the metal oxide.

24. The catalytic process of claim 1, wherein from 0 to 5 wppm water is present in the halide removal vessel.

25. The catalytic process of claim 1, wherein the contacted saturated hydrocarbon is the middle distillate or the base oil.

26. The catalytic process of claim 1, wherein the metal chloride catalyst comprises iron chloride, chromium chloride, zinc chloride, copper chloride or a mixture thereof.

* * * * *